United States Patent [19]

Commeyras et al.

[11] Patent Number: 4,540,792

[45] Date of Patent: Sep. 10, 1985

[54] PROCESS FOR THE PREPARATION OF A FREE L α-AMINO ACID

[75] Inventors: Auguste Commeyras, Clapiers; Aldo Previero; Martine Pugniere, both of Montpellier, all of France

[73] Assignees: Centre National de la Recherche Scientifique; Institut National de la Sante et de la Reserche Medicale, both of Paris, France

[21] Appl. No.: 472,479

[22] Filed: Mar. 7, 1983

[30] Foreign Application Priority Data

Mar. 23, 1982 [FR] France .................................. 82 04886

[51] Int. Cl.³ .................. C07D 233/64; C07D 209/20; C07D 207/16
[52] U.S. Cl. ...................................... 548/344; 548/498; 548/532; 548/535; 562/443; 562/445; 562/447; 562/557; 562/559; 562/560; 562/561; 562/562; 562/563; 562/564; 562/567; 562/570; 562/571; 562/573; 562/575
[58] Field of Search ............... 562/443, 445, 447, 557, 562/559, 560, 561, 562, 563, 564, 567, 570, 571, 573, 575; 548/344, 498, 532, 535

[56] References Cited

PUBLICATIONS

*Hackh's Chemical Dictionary,* 3rd Edition, Blakiston Co., Philadelphia, 1944, p. 101.
*Chemical Abstracts,* 90: 204451r (1979) [Dinelli et al., *Enzyme Eng.,* 1975, 3, 477–481].
*Chemical Abstracts,* 95: 95367y (1981) [Kazlauskas et al., *Polifermentn. Sist., Tezisy Soobshch. Vses. Semin.,* 1980, 2, 28–38].
*Chemical Abstracts,* 72: 32194u (1970) [Ando et al., *Bull. Chem. Soc. Jap.,* 1969, 42(9), 2624–2627].
*Chemical Abstracts,* 72: 32196w (1970) [Ando et al., *Bull. Chem. Soc. Jap.,* 1969, 42(9), 2628–2631].

*Primary Examiner*—Richard A. Schwartz
*Attorney, Agent, or Firm*—Dressler, Goldsmith, Shore, Sutker & Milnamow, Ltd.

[57] ABSTRACT

This invention relates to a process for the preparation of free L α-amino acids by the complete conversion of their D antipodes taken individually or possibly in racemic mixtures.

The process according to the present invention is characterized in that the D antipodes of an ester of said α-amino acid is racemized in the presence of a chemical catalyst formed by at least one aromatic aldehyde corresponding to the general formula:

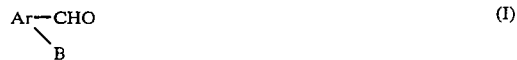

wherein:
Ar represents an aromatic ring optionally containing a heteroatom, such as nitrogen, and
B represents a basic function, to produce a mixture in dynamic equilibrium of the two forms D and L of said ester, the ester which is present in the L form is hydrolyzed enzymatically and irreversibly to produce the corresponding stereostable L α-amino acid, said stages of chemical racemization and of enzymatic hydrolysis being carried out under identical reaction conditions, and the free L α-amino acid is recovered.

24 Claims, No Drawings

PROCESS FOR THE PREPARATION OF A FREE L α-AMINO ACID

This invention relates to a process for the preparation of free L α-amino acids by the complete conversion of their D antipodes taken individually or optionally in racemic mixtures.

BACKGROUND OF THE INVENTION

The use of α-amino acids has recently developed to a considerable extent, in particular in the fields of medicine and nutrition, and the preparation of α-amino acids of the L series in particular is becoming more and more important.

At present, three main methods are known for the preparation of L α-amino acids. These are as follows:

1. The use of hydrolyzates of natural proteins, the limiting phase of which is the separation and the purification of each amino acid.
2. The fermentative method which, although more advantageous than the previous method, does not cover the production of all the desired α-amino acids.
3. Chemical synthesis which can produce simply and at a low cost large quantities of α-amino acids, but which has the disadvantage of producing substantially racemic mixtures.

The advantages and the profitability of this third method, which is certainly the most significant for the future from the economic point of view, are closely associated with the availability of general methods for the resolution of racemic mixtures.

Within this context, the introduction of enzymes into the technology of α-amino acids is presently a much more advantageous method than the conventional methods of physical or chemical separation. The enzymes which are presently used for this purpose may be exopeptidases, for example leucine amino peptidase (LAP) which, from the amide of a DL α-amino acid, only hydrolyses the L enantiomer. (R Koelsch, Enzymologia, 42,257(1972)).

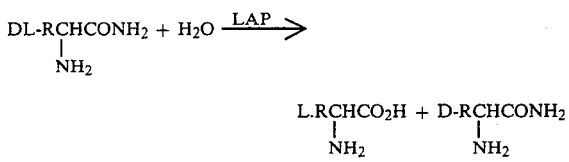

Carboxypeptidase has been used by a similar mechanism on the N-chloroacetyl derivatives of some amino acids (N. Grubhofer and L. Schleith, Naturwissenshaften, 40,508(1953)).

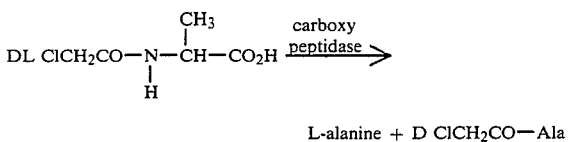

L-alanine + D ClCH$_2$CO—Ala

In these two examples, the yield of L isomer obviously cannot exceed 50%, since the D isomer is not recovered.

An improvement has been made to this enzymatic technique by coupling the action of the enzyme with a chemical type of racemization process (I. Chibata, T. Tosa, T. Sato and T. Mori, Methods in Enzymology, vol.44, p.746, Academic Press, 1976, and I. Chibata. T. Tosa, T. Sato, T. Mori and Y. Matuo, Proceedings of the IVth International Fermentation Symposium: Fermentation Technology Today, p.383, Society of Fermentation Technology, Japan, 1972).

The best known example concerns the use as enzyme of immobilized amino acylase which, from DL N-acetyl amino acids, exclusively hydrolyses the L isomer.

The L amino acid is then separated from the medium by crystallisation after the solvent has been concentrated.

The remaining D acetyl α-amino acid is then subjected to a treatment with acetic anhydride in an anhydrous medium which results in the formation of a DL 2-methyl 5-oxazoline. This is then hydrolysed to produce DL N-acetyl amino acid which is re-subjected to the action of amino acylase. By a continuous process, this system consequently leads to the complete recovery of the racemic mixture in the form of the L isomer.

In spite of the considerable progress which has been provided by this preparation method, the very great difference in concept should, however, be underlined in this process between the enzymatic catalysis which is used and the racemization stage of a non-catalytic chemical type which necessitates completely different experimental conditions. In effect, after the enzymatic hydrolysis stage which takes place in an aqueous solution, and after a first concentration which allows the separation of the L α-amino acid which has been produced, the water has to be completely removed and then replaced by acetic anhydride, a reagent which is consumed stoichiometrically in each racemization step. Then, before returning to the enzymatic step, the acetic acid formed in the medium has to be re-evaporated and replaced by water. Although this process is advantageous, it is very onerous from a technical and economic point of view.

SUMMARY OF THE INVENTION

This invention relates to a process for the preparation of L α-amino acids by the complete conversion of their D antipodes, either individually or in racemic mixtures, which makes it possible to rule out precisely these disadvantages. The process according to the present invention comprises introducing, cojointly with an enzymatic catalysis step, a chemical catalytic racemization step which is capable of being effected under the same reaction conditions (solvents, pH, temperature) as the enzymatic catalysis step.

Moreover, it should be noted that in the process which is an object of the present invention, the reagents are not consumed in the racemization stage. Moreover, the use of a single solvent makes it possible to envisage the realization of a continuous production system which is extremely simple and thus very economic.

The process of the present invention is characterised in that the D antipode of an ester of said α-amino acid is racemized in the presence of a chemical catalyst formed by at least one aromatic aldehyde corresponding to the general formula:

wherein:
Ar represents an aromatic ring optionally containing a heteroatom, such as nitrogen, and B represents a basic function,
to produce a mixture in dynamic equilibrium of the two forms D and L of said ester, the ester which is present in the L form is hydrolysed enzymatically in an irreversible manner to produce the corresponding stereostable L α-amino acid, said stages of chemical racemization and enzymatic hydrolysis being carried out under indentical reaction conditions, and the free L α-amino acid is recovered.

Other characteristics and advantages of the present invention will be revealed from reading the detailed description which follows.

DETAILED DESCRIPTION OF THE INVENTION

It is stated first of all that, while working on α-amino acids and on some of their derivatives, we have observed that some derivatives of α-amino acids and particularly the optically-active esters (of D configuration or of L configuration) are racemized when they are brought into the presence of some carbonyl compounds or a mixture of these compounds, and this occurs in various types of solvent, for example alcohols, notably lower aliphatic alcohols, such as methanol, ethanol, propanol and isopropanol, formamide, dimethylformamide, water or mixtures of these solvents.

An excellent racemization is also observed particularly in water and under physiological temperature and pH conditions in which the enzymes exhibit their maximum catalytic activity.

The following, in particular, are to be understood as physiological conditions:

a temperature of from 0° to 50° C., and more particularly from 20° to 40° C., and a pH of from 5 to 10, and more particularly from 6 to 9.

The aldehydes which are capable of being used as racemization catalysts for carrying out the process according to the present invention correspond to the general formula:

wherein:

Ar represents an aromatic ring optionally containing a heteroatom, such as nitrogen, and B represents a basic function.

The aromatic aldehydes which may be used within the scope of the present invention correspond in particular to the general formula:

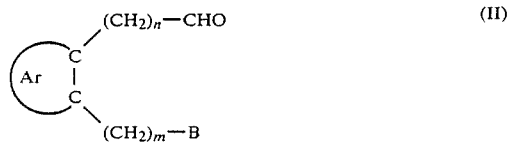

wherein:

Ar represents an aromatic ring containing from 5 to 7 members and optionally one hetero-atom, such as nitrogen, B represents a basic function such as tertiary amine or an anion derived from the ionisation of an acid function, such as $-CO_2^-$, $-OPO_3^{--}$, $-OPO_3H^-$ and $-SO_3^-$, and m and n represent integers from 0 to 5.

The most advantageous aldehydes for carrying out the process of the present invention are water-soluble aldehydes, notably the aldehydes corresponding to the general formulae I and II, wherein the aromatic fragment Ar, for example pyridine 2-aldehyde and pyridine 4-aldehyde, is functionalised by hydrophilic groups, such as —OH, —SO$_3$H or by other groups, such as lower $C_1-C_5$ alkyl radicals and lower $C_1-C_5$ hydroxyalkyl radicals.

More particularly, the present invention relates to a process involving an aldehyde corresponding to the following general formula as a racemization catalyst:

wherein: B represents a basic function, such as a tertiary amine or an anion derived from the ionisation of an acid function, such as $-CO_2^-$, $-OPO_3^{--}$, $-OPO_3H^-$ and $-SO_3^-$.

Pyridoxal-5'-phosphate and 5'-S-carboxymethylthiopyridoxal, which have proved to be perfectly suitable in their use as racemization catalysts, are mentioned as particular examples of these aldehydes corresponding to the general formula III. In solution, these two aldehydes are ionized respectively to produce the following anions:

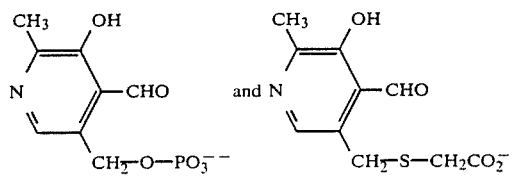

It should be noted that, among the aldehydes corresponding to the general formula III, some compounds such as pyridoxal-5'-phosphate are known, whereas others, such as 5'-S-carboxymethylthiopyridoxal are new. These new compounds may be obtained by carrying out processes similar to that which is mentioned in the following by way of example for the preparation of 5'-S-carboxymethylthiopyridoxal. The preparation method may be illustrated by the following reaction scheme.

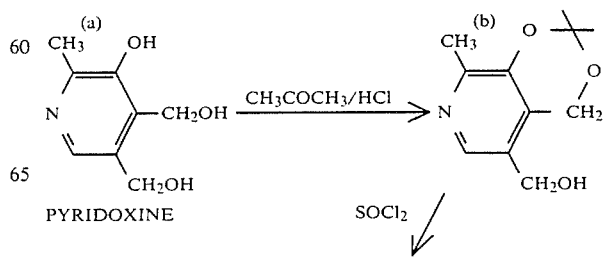

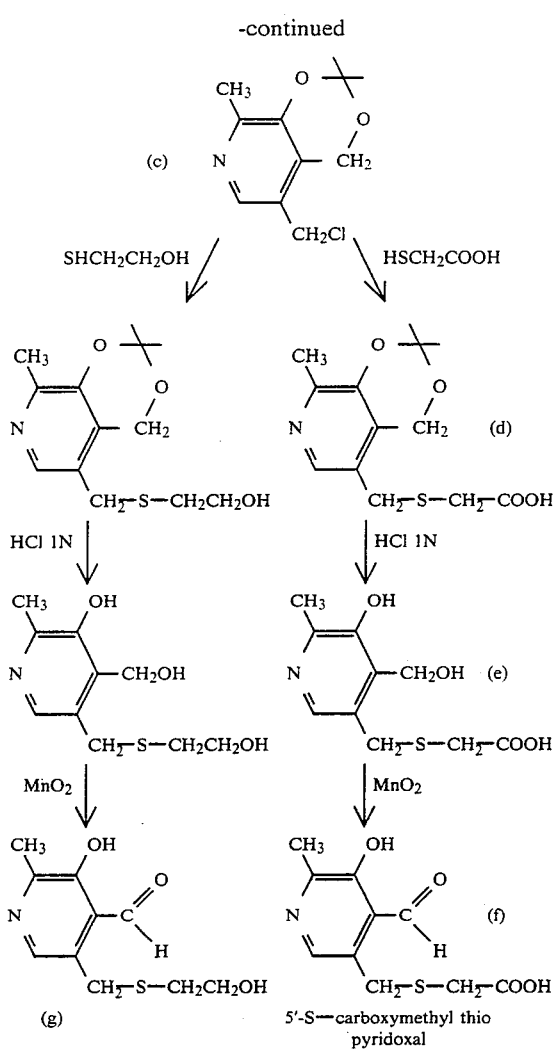

Synthesis of structural analogs of pyridoxal 5 g of vitamin B6 (pyridoxine) in the form of hydrochloride (a) are suspended in 250 ml of acetone. Gaseous hydrogen chloride is introduced into the mixture until the product has completely dissolved. The solution is left for 1 hour at ambient temperature in a stoppered Erlenmeyer flask, whereafter 3 volumes of ethyl ether are added. The cyclic ketal (b) precipitates immediately in the form of its hydrochloride and is then left to crystallise for one night at 5° C. The compound (b) is isolated by filtration, washed with ether and dried under vacuum at 40° C. up to constant weight. Yield 95%.

1 g of compound (b) is dissolved in 15 ml of SOCl₂ and left at ambient temperature for 1 hour.

The chlorinated derivative (c) is recovered in the form of a white powder after evaporation of the solvent and is kept under vacuum in the presence of soda in pastille form.

The yield of this operation is practically quantitative.

The chlorinated derivative (c) may react with different nucleophilic substances and thus constitutes the starting material for several syntheses. It has been found that mercaptans are the most reactive among the nucleophilic substances which have been studied and the scheme illustrates two synthesis examples.

Production of 5′-S-carboxymethylthiopyridoxal (f)

$10^{-3}$ mols of compound (c) in the form of the hydrochloride dissolved in 3 ml of methanol are added to $2 \times 10^{-3}$ mols of thioglycolic acid. 4 ml of N methanol in soda are added.

The NaCl starts to precipitate during the first minutes, and the reaction is left to continue for 3 hours at 50° C. After the NaCl has been removed by filtration, the filtrate is concentrated under reduced pressure and taken up by 5 ml of a mixture of CH₃OH:HCl (36%)=8:2. The solution is maintained at 50° C. for 3 hours. The NaCl is removed by filtration and the filtrate is evaporated to dryness under reduced pressure. The product (e) crystallises in the form of the hydrochloride by the addition of ethyl ether. yield 76%.

The compound (e) is dissolved in water to a concentration of $10^{-1}$M and is adjusted to pH 7 using soda. After the addition of MnO₂ [5 g for 1 g of product (e)], the suspension is left under vigorous agitation over a period of 4 to 5 hours at ambient temperature. MnO₂ is removed by centrifugation and the product (f) may be isolated after evaporation of the water or it may be used as it is in an aqueous solution.

The use of mercaptoethanol instead of thioglycolic acid leads through a similar synthesis to compound (g) which, however, has proved not to be very active during the racemization experiments.

Thus, we have found that these aromatic aldehydes and more particularly the structural analogs of pyridoxal corresponding to the general formula III may be used in a perfectly satisfactory manner as racemization catalysts, either in homogeneous phase, or in heterogeneous phase after immobilization on a support which is insoluble in the reaction medium. Immobilization of this type may be obtained by any known methods, such as by ionic bonds with anion exchanger resins or by covalent bonds which may be produced after adequate functionalization.

According to an additional characteristic of the present invention, the racemization catalyst formed by one or more aromatic aldehydes corresponding to formulae I, II or III is introduced into the reaction medium in a proportion of less than four times the stoichiometric quantity, and preferably less than once the stoichiometric quantity, with respect to the starting D α-amino acid ester.

We have observed in particular that under the previously defined reaction conditions (for example, in aqueous solution, between pH 7 and 8), in the presence of pyridoxal 5′-phosphate in a concentration equal to 0.1 mols per liter, the methyl esters of the D or L α-amino acids are racemized with ½ reaction times of from 2 to 10 minutes, at a temperature of 20° C. and for a concentration of pyridoxal-5′-phosphate which is substantially equal to that of the ester.

A racemization of this type has been obtained in particular with methyl esters of alanine, arginine, aspartic acid, asparagine, glutamic acid, glutamine, leucine, lysine, β-phenyl alanine, serine, tyrosine, tryptophane, cystine and methionine.

The esters which are capable of being subjected to the first stage of chemical catalytic racemization mainly consist of alkyl esters which are optionally activated, such as thioesters, the α-amino acids being used either in the form of their D antipodes, or in racemic mixtures. They may be used in the form of free bases or as salts.

It has also been observed that the rate of racemization may depend on the chemical nature of the ester. For example, it decreases in passing from the methyl ester to the ethyl and isopropyl esters.

Moreover, we have observed that the rate of racemization is also an increasing function of the concentration of aldehyde. The racemization rate decreases for a concentration of aldehyde which is clearly lower than that of the ester of the α-amino acid, but all of the ester of the α-amino acid is nevertheless racemized, which fact demonstrates the catalytic power of aldehyde in the process for the racemization of esters of the α-amino acids.

It should also be noted that the free α-amino acids, unlike the esters of a α-amino acids, are not racemized in the presence of aldehyde under the same reaction conditions. This is of paramount importance, as will be seen later on for the rest of the process.

Finally, care must be taken that metallic cations, such as those derived for example from the following metals: Mg, Ca, Bu, Zn, Cd, Hg, Sn, Pb, Mn, Fe, CO, Ni, Cu and Al, are not present in the reaction medium so that the free α-amino acids in turn are not able to be racemized or deaminated.

In accordance with these various observations, we propose to explain the chemical catalytic racemization by the following mechanism although no restriction to this interpretation should be implied:

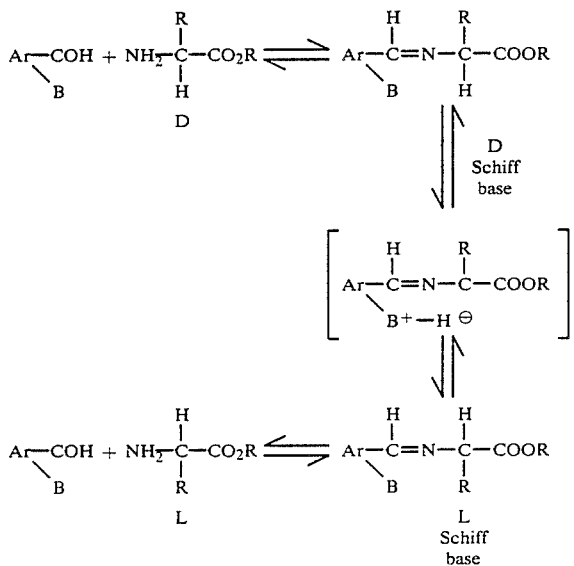

The intermediary which may be envisaged is the passage through a carbanion which is doubly favoured, on the one hand by its conjugation with the carbonyl function of the ester and the imine function, and on the other hand by the intramolecular assistance of the basic function (B) which labilizes the proton of the asymmetric carbon.

The importance of this basic function is demonstrated, moreover, by the observation of a clear difference in catalytic efficiency of the compounds (f) and (g) from the scheme given above:

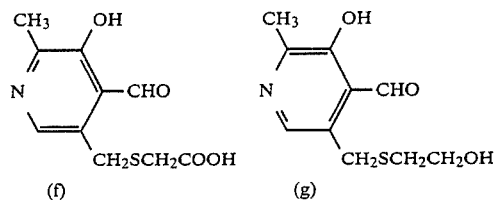

In effect, the replacement of the —COO⁻ function by the CH₂OH function, which is considerably less basic, means that the compound (g) becomes considerably less active from a catalytic point of view compared to the compound (f). This clearly illustrates the importance of the bifunctional catalysis in the racemization phenomenon.

The aldehydes having such a general structure are considered as bifunctional catalysts associating the aldehyde function, which results in the Schiff base of the amino acid ester, and the basic function which is responsible for the formation of the carbanion, the racemization intermediate.

However, the basic catalysis which demonstrates its maximum efficiency in an intramolecular mechanism may also be discerned in an intermolecular mechanism.

In effect, we have observed that the rate of racemization of amino acid esters in the presence of a single aromatic aldehyde (for example an analog of pyridoxal free from a basic function) may be substantially increased by the presence in the reaction medium of a basic function, such as a carboxylate anion (sodium acetate or trialkyl ammonium acetate). The temperature and pH conditions remain constant during these experiments.

Finally, it will be noted that in the case of the free α-amino acids, the absence of the ester function is sufficient to prevent any migration of the proton bound to the asymmetric carbon.

According to this scheme, some of the ester of the α-amino acid is blocked in the form of a Schiff base in a proportion which is a function of its concentration ratio with the catalyst.

From an economic point of view, the ratio between catalyst and ester will have to be the result of a compromise between an adequate racemization rate (all the faster because a greater concentration of ester is trapped in the form of a Schiff base) and the necessity of having a considerable concentration of free ester present in the equilibrium so that this may be subjected to enzymatic hydrolysis (as will be seen later on).

Now that this racemization process has been observed and explained, it is noted that the esters of the α-amino acids which are concerned may be considered as substrates for certain enzymes.

Moreover, the conditions under which the racemizations function strictly coincide with those which are generally required for the operation of the enzymes.

In fact, it is known that certain carboxyl derivatives of α-amino acids, including the esters, may be hydrolysed to produce free α-amino acids by enzymatic catalysis. Some of these enzymes are endowed with a high chirality and they only hydrolyse the L isomers while leaving unchanged the D antipodes which are present.

We have observed that such an enzymatic catalysis, coupled with the racemization catalysis as previously defined, applied to the esters of α-amino acids, either of D configuration or of L configuration, or of a mixture of the two antipodes in any ratio, results in every case in the single production of the free α-amino acid of the L series in a quantitative yield with respect to the starting α-amino acid ester.

The quantitative yield of this process is explained by the fact that the substrate of the enzymatic reaction is in a racemization equilibrium, whereas the product of the reaction which is formed in an irreversible manner is stereostable under the same conditions and may thus accumulate.

The general operating principle of the system may then be simplified as follows:

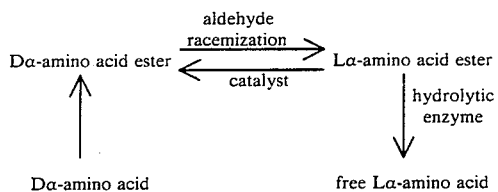

In this general scheme illustrating the configuration rectification, the first step is the esterification of the D, L or DL α-amino acids, for which a certain number of reagents which are already known are available, such as alcohol mixed with an acid catalyst, or methyl sulphate or dimethyl sulphite.

From the esters, the two types of catalysis which are implied: the racemization catalysis which produces the substrates for the enzyme, and the enzymatic catalysis which follows, may obviously act together in a homogeneous system. Nevertheless, although this method of operation is the simplest to carry out, it has some disadvantages, the greatest of which is the separation of the free α-amino acids and the recovery of the catalysts.

Moreover, the chemical reaction which is possible between the racemization catalyst(s) and certain functional groups of the enzymes may result in a loss of activity of the catalysts, and may also result in a modification in the catalytic activity of the enzyme.

For these reasons, it is preferable to use these two catalysts while keeping them separate in the reaction medium by immobilization, for example by fixation on supports which are insoluble in the reaction medium.

The insoluble supports carrying the two catalysts may be used as a material for filling two separate reactors which are connected by a system for the circulation of the liquid medium.

A more simplified system comprises mixing the two insoluble supports carrying the two catalysts with the reaction media in a single reactor.

Given the consecutive natures of these two types of catalysis, a model of a reactor which may be envisaged could also comprise an assembly of layers of the two immobilized catalysts which are piled up in an alternating manner in a circulation reactor.

The enzymes will be immobilized by any methods of the art, and likewise the aldehyde racemization catalysts.

The supports which are used for fixing the aldehyde racemization catalyst when carrying out the process of the present invention have been anion exchange resins, such as diethylaminoether Sephadex ®, diethylaminoethyl cellulose or resins having polystyrene matrices carrying quaternary ammonium. The pyridoxal phosphate is attached for example, in a completely ionic manner onto such resins within the pH range which is used and which has previously been defined.

The enzymes which are used in this process have either been in a homogeneous phase, or attached to supports which are insoluble in the reaction medium, to a polyacrylic matrix or to a polysaccharide matrix.

In these reactions, the insoluble supports and the fixation methods are mentioned by way of example and are in no way limiting.

The enzymes which may be most commonly used in the process of the present invention are hydrolytic enzymes, such as trypsin, α-chymotrypsin, papain, chymopapain, and leucine amino peptidase. This list is in no way limiting. The particular choice of these enzymes depends on their specificity with respect to the α-amino acid to be prepared.

Although the essential aim of this process is the production of L α-amino acids from racemic mixtures, it may also allow, from α-amino acids which are optically active or optically inactive, the substitution of the proton carried by the α carbon by a deuterium or a tritium by working in heavy water or tritiated water.

The following Examples illustrate the process of the present invention without, however, restricting it.

EXAMPLES OF RACEMIZATION IN HOMOGENEOUS PHASE

In a standard experiment, to a $10^{-1}$ molar aqueous solution of an ester of L or D α-amino acid in the form of the hydrochloride, adjusted to pH 7 by the addition of soda, there is added an equal volume of an aqueous solution of pyridoxal-5'-phosphate (pH 7) of a molarity lower than or equal to that of the ester of the α-amino acid. The temperature is maintained constant at the desired value, for example at 20° C.

The rotating power of the solution is continuously followed at 546 nanometers by means of a micropolarimeter. When this rotating power is zero (in variable ½ reaction times depending on the temperature and on the concentration ratio of ester:pyridoxal), the reaction medium is analysed by thin layer chromatography and is compared to the starting solution to check that the ester function has not been chemically hydrolysed.

The results concerning a certain number of α-amino acids are given in the following Table.

| Example No. | Methyl esters of | $R = \frac{[\text{pyridoxal 5' phosphate}]}{[\text{ester of } \alpha\text{-amino acid}]} = 1$ t ½ (min) of racemization | $R = \frac{[\text{pyridoxal 5' phosphate}]}{[\text{ester of } \alpha\text{-amino acid}]} = 0.5$ t ½ (min) of racemization |
|---|---|---|---|
| 1 | Alanine | 3.9 | 5.1 |
| 2 | Leucine | 6.6 | 14 |
| 3 | α-phenyl-alanine | 3.8 | 9.6 |
| 4 | Tyrosine | 12.1 | 30.39 |
| 5 | Methionine | 16.7 | 10.5 |

-continued

| Example No. | Methyl esters of | $R = \dfrac{[\text{pyridoxal 5' phosphate}]}{[\text{ester of }\alpha\text{-amino acid}]} = 1$ $t\frac{1}{2}$ (min) of racemization | $R = \dfrac{[\text{pyridoxal 5' phosphate}]}{[\text{ester of }\alpha\text{-amino acid}]} = 0.5$ $t\frac{1}{2}$ (min) of racemization |
|---|---|---|---|
| 6 | Lysine | 4.62 | 13.4 |
| 7 | Glutamic | 8.1 | 17.9 |
| 8 | Aspartic | 4.2 | 10.4 |
| 9 | Leucine ethyl ester | 9.02 | |
| 10 | Leucine isopropyl ester | 10.07 | |

EXAMPLES OF RACEMIZATION IN HETEROGENEOUS PHASE AND ENZYMATIC RESOLUTION OF THE RACEMIC MIXTURE

Example 11

In a standard experiment, pyridoxal-5'-phosphate in $0.5 \cdot 10^{-2}$ molar solution in water is adjusted to pH 7 to constitute a mother solution.

50 microliters of this solution are diluted in 3 ml of acetate buffer (pH 5.4) and the optical density is measured at 400 nm for a control. 3 g of diethylaminoethyl cellulose resin are then added to 20 ml of the mother solution and the suspension is maintained at pH 7 under agitation.

After 5 minutes, the suspension is decanted and 50 microliters of supernatant are removed and analysed spectrally at 400 nm under the previously mentioned conditions. The zero optical density which is observed indicates that the pyridoxal-5'-phosphate is completely fixed to the support. D tyrosine methyl ester is then added to the solution thus obtained to produce a final concentration of $10^{-2}$ molar. The suspension is maintained under vigorous agitation at a constant temperature equal to 20° C.

Series of three samples are then removed at regular time intervals:

the first sample is analysed by automatic analysis and it shows that there is no trace of free α-amino acid in the medium.

The second sample after suitable dilution is analysed spectrophotometrically (λmax. 274 nm) to permit determination of the concentration of free tyrosine methyl ester which is the only chromophore present in the supernatant (the missing part remaining attached to the catalyst).

The third sample is subjected to chymotrypsic hydrolysis which only releases L α-amino acid from the corresponding ester.

The results which are obtained are indicated in the following Table:

| t min | fixed tyrosine ester in % | free tyrosine ester in % | racemization in % | liberated L tyrosine |
|---|---|---|---|---|
| 5 | 0.49 | 0.51 | 14 | 7 |
| 10 | " | " | 16 | 8 |
| 20 | " | " | 47 | 23.5 |
| 40 | " | " | 75 | 37.5 |
| 80 | " | " | 93 | 46.5 |
| 160 | " | " | 100 | 50 |

Example 12

The following results are obtained by using the same experimental procedure as in Example 11, but at a temperature of 40° C.:

| t min | fixed tyrosine methyl ester in % | free tyrosine methyl ester in % | racemization in % | liberated L tyrosine % |
|---|---|---|---|---|
| 5 | 0.49 | 0.51 | 95 | 47.5 |
| 10 | " | " | 100 | 50 |
| 80 | " | " | 100 | 50 |

Example 13

5'-S-carboxymethylthiopyridoxal: racemization in homogeneous phase and enzymatic resolution of the racemic mixture.

5 ml of a $10^{-2}$M aqueous solution of 5'-S-carboxymethylthiopyridoxal, adjusted to pH 7, are added to 5 ml of a $5 \times 10^{-2}$M aqueous solution of D-phenylalanine methyl ester at pH 7. The mixture is maintained under agitation at a temperature of 20° C. At the desired times (see the table), 1 ml of the reaction mixture is diluted with 1 ml of 5% NaHCO$_3$ in water and extracted using 2 ml of ethyl acetate saturated with water. This procedure allows a clean separation of the racemization catalyst which remains in the aqueous phase, while the organic phase contains the ester of the α-amino acid.

A fraction of the organic phase is evaporated, subjected to acid hydrolysis and analysed in an automatic α-amino acid analyser. This operation makes it possible to quantitatively determine the ester of the α-amino acid which is separated by extraction.

Another fraction is evaporated and treated with α-chymotrypsin: the phenylalanine which is released is analysed in an automatic analyser. This last analysis makes it possible to determine the fraction of L isomer which is present in the mixture (the only one to be digested).

Chromatographic controls have shown the absence of free phenylalanine in the starting ethyl acetate phase.

The results which are obtained are provided in the following Table.

| racemization time (min) | L-phenylalanine formed (%) | racemization rate (%) |
|---|---|---|
| 20 | 25 | 50 |
| 80 | 36 | 72 |

EXAMPLES OF RECTIFICATION OF CONFIGURATION

Example 14

Pyridoxal-5'-phosphate is immobilised as described in Examples 11 and 12 at a concentration identical to that described in Example 11 (20 ml of $0.5 \cdot 10^{-2}$ molar solution plus 3 g of diethylaminoethyl cellulose resin, i.e. 0.1 milliequivalent).

50.9 mg of D tryptophane methyl ester are added to this solution in the form of the hydrochloride (0.2 milliequivalents). The pH is adjusted to 7 and the temperature is maintained at 40° C.

20 mg of chymotrypsin are then added to this solution.

After reaction for 30 minutes, the pyridoxal phosphate fixed on the support is separated from the medium by filtration. The volume of supernatant is measured, and found to be 17 ml.

An aliquot part is subjected in a first time to two analyses:

1. Chromatography demonstrates the complete disappearance of the α-amino acid ester, and the sole presence in the liquid phase of the free α-amino acid.

2. A second quantitative analysis on an auto-analyser indicates that the quantity of free tryptophane which is present in the separated supernatant is equal to 40% of the molar quantity of ester which was initially introduced into the medium (the remaining 60% are considered to be fixed to the support directly and through the catalyst as well as in the liquid phase bathing the support).

17 ml of water and 16.5 mg of D tryptophane methyl ester (equivalent to the quantity of trytophane which was previously hydrolysed) plus 10 mg of chymotrypsin are then added to the solid phase containing the racemization catalyst.

After a new reaction time of 30 minutes at 40° C., the two phases are again separated. The free acid tryptophane is determined. The conversion rate of this reaction:

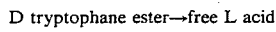

D tryptophane ester→free L acid is quantitative when compared to the last addition.

The supernatant is lyophilized and the free α-amino acid is purified by filtration on Sephadex ®G 25 equilibrated with 1% acetic acid.

The fraction containing the α-amino acid is re-lyophilized and the α-amino acid is esterified by the methanol-thionyl chloride method at ambient temperature.

The ester thus obtained in re-subjected to chymotrypsic hydrolysis in the absence of pyridoxal phosphate. All of the ester is rapidly hydrolysed to produce free α-amino acid, which demonstrates that it belongs to the L series.

Parallel experiments carried out on the esters of D α-amino acids did not provide any trace of free α-amino acid under comparable conditions.

Example 15

D tyrosine methyl ester was treated in the same way as D tryptophane of Example 14.

The recovery yield of L tyrosine after the first stage amounted to 42%.

The replacement of this first fraction of L tryosine by an equivalent quantity of D tyrosine ester on the same catalyst produced a quantitative conversion into L tyrosine under the same operational conditions as those of Example 14.

The steric series of the α-amino acid was controlled as previously described.

Example 16

D phenylalanine methyl ester under the same operational conditions as for Example 14 produces 39% of L phenylalanine at the first addition (61% remaining reversibly fixed to the support).

The second addition is converted quantitatively as well as a third addition. This demonstrates the possibility of the continuous operation of the system.

Of course, the present invention is not restricted to the particular practical Examples which have been described. On the other hand, it is quite possible, without thereby departing from the scope of the present invention, to envisage some variants, in particular concerning the choice of ester subjected to racemization and of the aldehyde catalysing the racemization. The process of the present invention makes it possible in a very general manner to ensure the rectification of the configuration of D antipodes of various α-amino acids, such as alanine, valine, leucine, isoleucine, β-phenylalanine, serine, threonine, lysine, δ-hydroxylysine, arginine, aspartic acid, asparagine, glutamic acid, glutamine, cysteine, cystine, methionine, tyrosine, thyroxine, proline, hydroxyproline, tryptophane and histidine.

We claim:

1. A process for the preparation of a free Lα-amino acid, which comprises racemizing the D antipode of an ester of said α-amino acid in the presence of a chemical catalyst formed by at least one aromatic aldehyde corresponding to the formula:

wherein:
  Ar represents an aromatic ring optionally containing a heteroatom, and
  B represents a basic function of the group consisting of tertiary amines and anions derived from the ionisation of an acid function,
to produce a mixture in dynamic equilibrium of the two forms D and L of said ester; hydrolysing the ester which is present in the L form enzymatically and irreversibly to produce the corresponding stereostable Lα-amino acid, said steps of chemical racemization and of enzymatic hydrolysis being carried out under identical reaction conditions; and recovering the free Lα-amino acid.

2. A process according to claim 1, wherein said heteroatom is nitrogen.

3. A process according to claim 1, wherein said aromatic aldehyde corresponds to the formula:

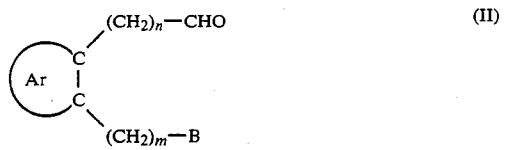

wherein:

Ar represents an aromatic ring containing from 5 to 7 members and optionally containing a heteroatom, B represents a basic function of the group consisting of tertiary amines and anions derived from the ionisation of an acid function, and m and n represent integers from 0 to 5.

4. A process according to claim 3, wherein said heteroatom is nitrogen.

5. A process according to claim 1, wherein said acid function is $-CO_2^-$, $-OPO_3^{--}$, $-OPO_3H^-$ or $-SO_3^-$.

6. A process according to claim 1, wherein said aromatic aldehyde corresponds to the formula:

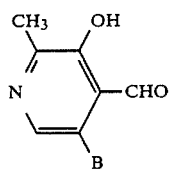

(III)

wherein: B represents a basic function of the group consisting of tertiary amines and anions derived from the ionisation of an acid function.

7. A process according to claim 6, wherein said acid function is selected from $-CO_2^-$, $-OPO_3^{--}$, $-OPO_3H^-$ and $-SO_3^-$.

8. A process according to claim 6, wherein said aromatic aldehyde corresponds to formula III, wherein the basic function B represents the group $-CH_2-O-PO_3^{--}$.

9. A process according to claim 6, wherein said aromatic aldehyde corresponds to formula III wherein the basic function B represents the group $-CH_2-S-CH_2-CO_2^-$.

10. A process according to claim 1, wherein the chemical racemization catalyst which is formed by said at least one aromatic aldehyde is introduced into the reaction medium in a proportion of less than four times the stoichiometric quantity with respect to the ester of the D α-amino acid.

11. A process according to claim 10, wherein said proportion is less than once said stoichiometric quantity.

12. A process according to claim 1, wherein the chemical racemization catalyst is fixed on a support which is insoluble in the reaction medium.

13. A process according to claim 1, wherein the steps of chemical racemization and of enzymatic hydrolysis are carried out in a solvent selected from among alcohols, formamide, dimethylformamide and water, as well as mixtures of these solvents.

14. A process according to claim 1, wherein the steps of chemical racemization and of enzymatic hydrolysis are carried out in a reaction medium, the pH of which is from about 5 to about 10.

15. A process according to claim 14, wherein the pH is from 6 to 9.

16. A process according to claim 1, wherein the steps of chemical racemization and of enzymatic hydrolysis are carried out in a reaction medium, the temperature of which is from about 0° to about 50° C.

17. A process according to claim 16, wherein said temperature is from 20° to 40° C.

18. A process according to claim 1, wherein the starting ester of the α-amino acid is introduced into the reaction medium in the form of a racemic mixture.

19. A process according to claim 1, wherein the starting ester of the α-amino acid which is used is selected from among methyl, ethyl, propyl, and isopropylesters, in the form of a free base or in the form of a salt.

20. A process according to claim 1, wherein the enzymatic hydrolysis step is effected using an esterase.

21. A process according to claim 20, wherein said esterase is selected from trypsin, chymotrypsin, papain, chymopapain and leucine amino peptidase.

22. A process according to claim 20, wherein said esterase is fixed on a support which is insoluble in the reaction medium.

23. A process according to claim 1, wherein the starting ester of the D α-amino acid is obtained, by known means, from the D α-amino acid.

24. A process according to claim 1, comprising the preparation of the L antipode of an α-amino acid selected from among the following: alanine, valine, leucine, isoleucine, β-phenylalanine, serine, threonine, lysine, δ-hydroxylysine, arginine, aspartic acid, asparagine, glutamic acid, glutamine, cysteine, cystine, methionine, tyrosine, thyroxine, proline, hydroxyproline, tryptophane and histidine.

* * * * *

UNITED STATES PATENT AND TRADEMARK OFFICE
CERTIFICATE OF CORRECTION

PATENT NO. : 4,540,792
DATED : September 10, 1985
INVENTOR(S) : AUGUSTE COMMEYRAS, ALDO PREVIERO AND MARTINE PUGNIERE It is certified that error appears in the above-identified patent and that said Letters Patent is hereby corrected as shown below:

Column 1, line 41, the "42" of number 42,257 should be underlined and similarly at Column 1, line 53, the "40" of number 40,508 should be underlined.

Column 13, line 52 "in" should be --is--.

Column 14, line 13, "the system" should be --this system--.

Signed and Sealed this

Third Day of December 1985

[SEAL]

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,540,792
DATED : September 10, 1985
INVENTOR(S) : Auguste Commeyras, Aldo Previero, Martine Pugniere It is certified that error appears in the above-identified patent and that said Letters Patent is hereby corrected as shown below:

Title page, left-hand column, in the name of the second assignee, "Reserche" should be --Recherche--

Signed and Sealed this

Fourteenth Day of October, 1986

[SEAL]

Attest:

Attesting Officer

DONALD J. QUIGG

Commissioner of Patents and Trademarks